United States Patent [19]
Yokoi et al.

[11] Patent Number: 5,125,411
[45] Date of Patent: Jun. 30, 1992

[54] ULTRASOUND DIAGNOSTIC APPARATUS FOR USE IN A BODY CAVITY

[75] Inventors: Takeshi Yokoi, Hino; Kazuya Saiga; Kenji Hirooka, both of Hachioji, all of Japan

[73] Assignee: Olympus Optical Co., Ltd., Tokyo, Japan

[21] Appl. No.: 648,201

[22] Filed: Jan. 31, 1991

[30] Foreign Application Priority Data

| Apr. 9, 1990 | [JP] | Japan | 2-92318 |
| Jun. 22, 1990 | [JP] | Japan | 2-162924 |
| Nov. 8, 1990 | [JP] | Japan | 2-303288 |

[51] Int. Cl.$^5$ .............................................. A61B 8/14
[52] U.S. Cl. ..................... 128/662.06; 128/660.09
[58] Field of Search ............... 128/660.01, 660.09, 128/662.06, 677

[56] References Cited

U.S. PATENT DOCUMENTS

| 3,929,129 | 12/1975 | Archambault | 128/677 |
| 4,139,000 | 2/1979 | Peeler | 128/677 |
| 4,466,443 | 8/1984 | Utsugi | 128/662.06 |
| 4,588,706 | 12/1985 | Nakada et al. | 128/660.01 |
| 4,779,624 | 10/1988 | Yokoi | 128/662.06 |
| 4,807,634 | 2/1989 | Enjoji et al. | 128/660.01 |
| 4,957,112 | 9/1990 | Yokoi et al. | 128/662.06 |

*Primary Examiner*—Francis Jaworski
*Assistant Examiner*—George Manuel
*Attorney, Agent, or Firm*—Frishauf, Holtz, Goodman & Woodward

[57] ABSTRACT

An ultrasound probe is located in a chamber defined in a housing to be inserted into a body cavity of a subject. A drive shaft is connected to the probe to transmit a rotational force and, for this purpose, is coupled to a drive source via a passage of an insertion section of an ultrasound diagnostic apparatus. A first sealing member is provided for blocking a communication between the chamber and one end of the passage, a second sealing member is provided for sealing the other end of the passage of the guide member, and a bypass communication passage is provided for enabling the passage to communicate with the chamber. An opening/closing valve is provided for opening and closing the communication passage via which an ultrasound transmitting medium is filled in the chamber and the passage of the insertion passage. The communication passage is blocked after the filling operation has been done.

10 Claims, 14 Drawing Sheets

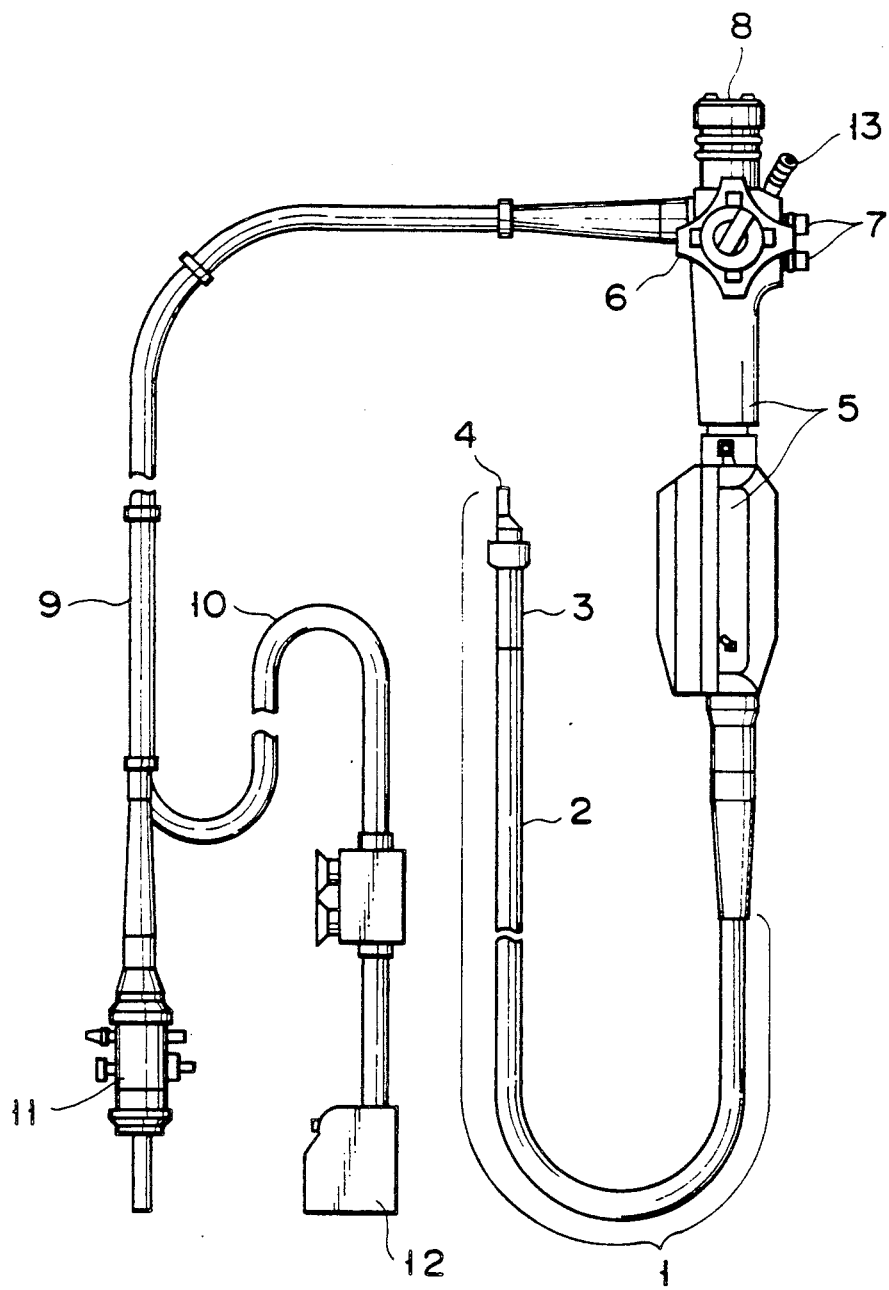
F I G. 1

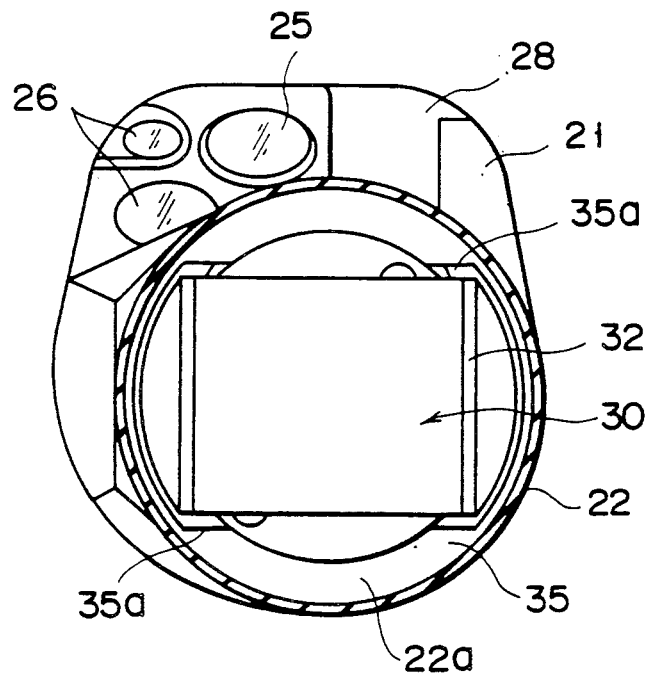
FIG. 4
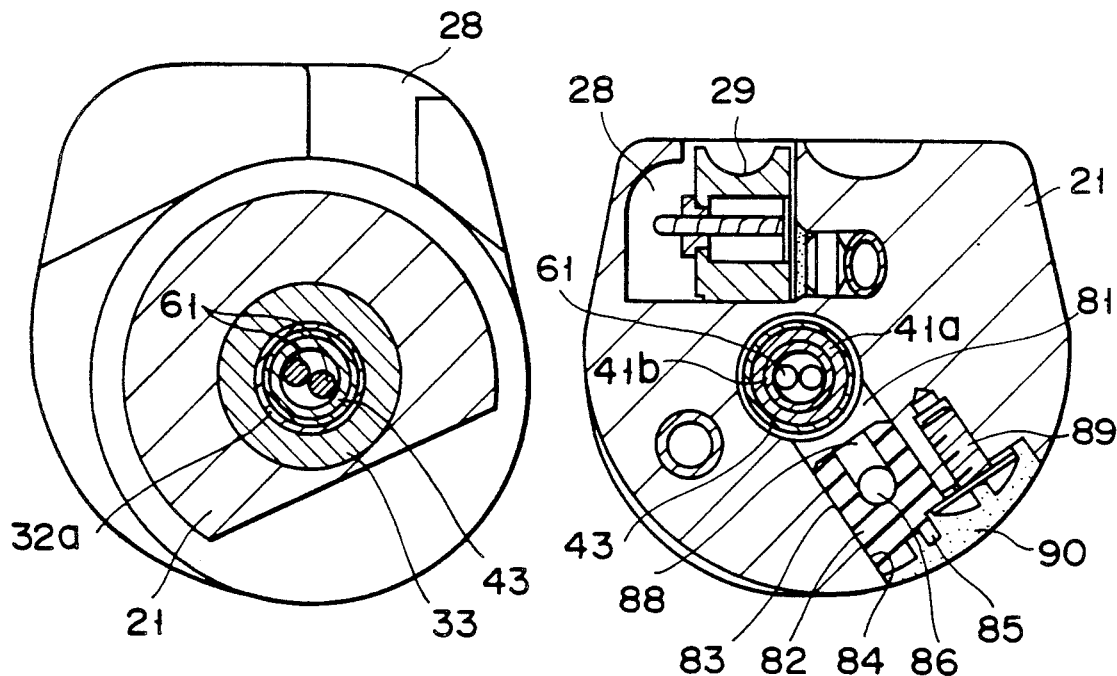
FIG. 5
FIG. 6

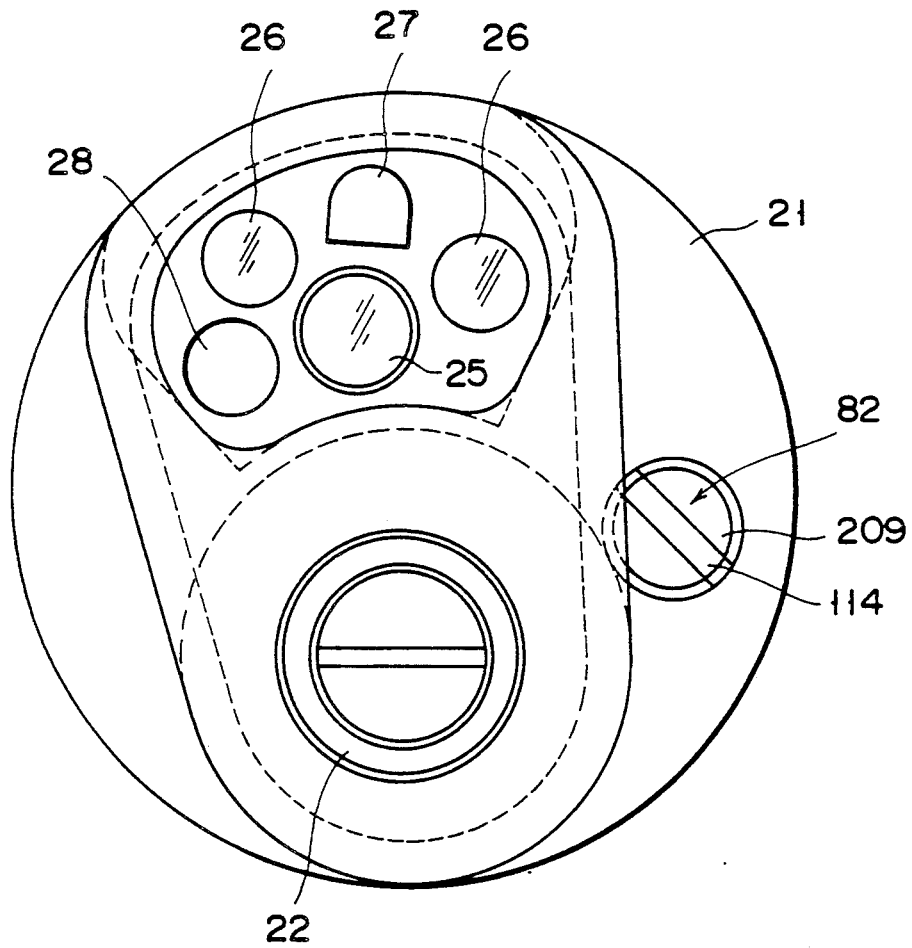
F I G. 15

ULTRASOUND DIAGNOSTIC APPARATUS FOR USE IN A BODY CAVITY

BACKGROUND OF THE INVENTION

1. Field of the Invention

The present invention relates to an ultrasound diagnostic apparatus which can obtain an ultrasound observation image of a body tissue through a mechanical scanning by an ultrasound probe inserted in the body cavity of a human being.

2. Description of the Related Art

In this type of ultrasound diagnostic apparatus, two ultrasound beam scanning systems are known: an electronic and a mechanical system. As known in Published Unexamined Japanese Patent Application No. 57-168648, the apparatus using a mechanical system is of such a type that a probe for transmitting and receiving an ultrasound is rotatably provided in a chamber defined by an insertion section tip cover of an instrument, and connected to a flexible drive shaft passing through the insertion section's channel. A rotational force of a motor on an operation side of the instrument is transmitted via the drive shaft to the ultrasonic probe. By so doing, the ultrasound probe is rotated to change the direction of its transmitting ultrasound beam and that of its receiving echo in its scanning motion.

An ultrasound transmitting medium is filled in the chamber set out above. The interior of the chamber communicates with the channel through which the drive shaft passes with the ultrasound transmitting medium filled in a resultant communication space provided by the two.

The drive shaft is formed of a tightly coiled metal wire and has its own flexibility. When, therefore, the ultrasound transmitting medium is filled in the communication space, tiny air bubbles are liable to stay trapped between the wire turned portions and in the coil's interior. The resultant structure, if being assembled in such a situation, allows the air bubbles to gradually enter the chamber where the transmitting/receiving probe is located. With the air bubbles so intruded in the chamber, the ultrasonic beam transmitted and received by the probe is scattered or damped by the air bubbles, failing to obtain a better transmission and reception of the ultrasonic wave.

Further, dust is also produced due to, for example, the frictional contact of the rotating drive shaft in use with a channel member and enters the chamber via the channel. The dust causes the scattering or damping of the transmitting and receiving ultrasonic beam, failing to obtain a better ultrasonic image.

In order to solve this problem, a proposal is made to provide an air bubble trap between a chamber and a channel as disclosed in U.S. Pat. No. 4,807,634 (corresponding to Published Unexamined Japanese Patent Application No. 62-201145).

The provision of the air bubble means cannot completely avoid the entry of the air bubbles and dust.

In order to overcome this inconvenience, Published Unexamined Japanese Patent Application No. 58-152547 proposes to provide a sealing member between a chamber having an ultrasonic probe therein and a channel through which a drive shaft passes whereby air bubbles are prevented from entering the chamber.

The use of the sealing member has a drawback in that it is not possible to fill a ultrasound transmitting medium from the chamber side while preventing the ingress of air bubbles into the chamber, by the use of suction from a guide passage, so that they do not remain in the chamber. Further, the sealing member is provided immediately behind the chamber and it is difficult to fill the ultrasound transmitting medium into the guide passage from behind the sealing member. Since the guide passage normally provides a space where air is occupied, there is a risk that the drive shaft will not be smoothly rotated in the guide passage due to a lack of adequate lubrication relative to the drive shaft.

In use an instrument's insertion section is bent and, therefore, the drive shaft is rotated in a manner to be intensely in frictional contact with the inner surface of a tube for guide passage. A pliable material, such as polyurethane or teflon, of which the guide tube is made, wears out due to a lack of adequate lubrication on the drive shaft, causing many tiny particles originating from the wear to float in the passage.

The sealing member shuts off a communication between the chamber and the guide passage and, as a whole air layer occupies a location behind the sealing member, "breathing" occurs between the interior of the chamber and the guide passage eve if a slight pressure differential is developed across the chamber interior and the passage. This causes a gradual ingress into the chamber of the air bubbles and particles originating from the wear, disturbing an ultrasonic image and hence offering a bar to diagnosis.

SUMMARY OF THE INVENTION

It is accordingly the object of the present invention to provide an ultrasound diagnostic apparatus which can readily fill an ultrasound transmitting medium into a chamber with an ultrasonic probe held therein and into a passage through which a drive shaft passes and can protect an ingress of air bubbles and foreign matter, such as dust, from a guide passage side, whereby it is possible to obtain a better ultrasonic image.

According to the present invention, there is provided an ultrasound diagnostic apparatus which is inserted into a body cavity of a subject and mechanically scans the body cavity of interest with an ultrasound beam, to obtain an ultrasound observation image of a organ subject which comprises:

(a) an elongated insertion section including a distal end portion to be inserted into the body cavity of the subject, having a housing with a chamber defined therein, a proximal end portion, and a guide passage extending along the length of the insertion section and having one end leading to the chamber and the other end;

(b) a probe for ultrasound conversion which has a rotation axis around which it is rotatable in the chamber;

(c) a drive shaft having one end connected to the probe to transmit a rotational force to the probe, and the other end;

(d) a drive source connected to said other end of the drive shaft;

(e) first sealing means for blocking a communication between the chamber and the one end of the guide passage;

(f) second sealing means for sealing the other end of the guide passage;

(g) a bypass communication passage for allowing a communication between the chamber and the guide passage;

(h) means provided at the bypass communication passage and adapted to selectively open and close the bypass communication passage; and (i) an ultrasound transmitting medium filled in the chamber and the guide passage.

According to the present invention, air bubbles and foreign matter, such as dust, are prevented from entering the chamber with an ultrasound probe contained therein, thus obtaining a better ultrasonic image. Further, the bypass communication passage is opened by the communication passage opening/closing means and the filling of the ultrasound transmitting medium is achieved. After this is done, the chamber can be positively sealed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a view showing an ultrasound diagnostic apparatus according to a first embodiment of the present invention;

FIG. 4 is a cross-sectional view, as taken along line A—A in FIG. 2;

FIG. 5 is a cross-sectional view, as taken along line B—B in FIG. 2;

FIG. 6 is a cross-sectional view, as taken along line C—C in FIG. 2;

FIG. 15 is a front view showing the distal end portion of the insertion section of the fourth embodiment of FIG. 14;

DETAILED DESCRIPTION OF THE PREFERRED EMBODIMENTS

Figure 2:
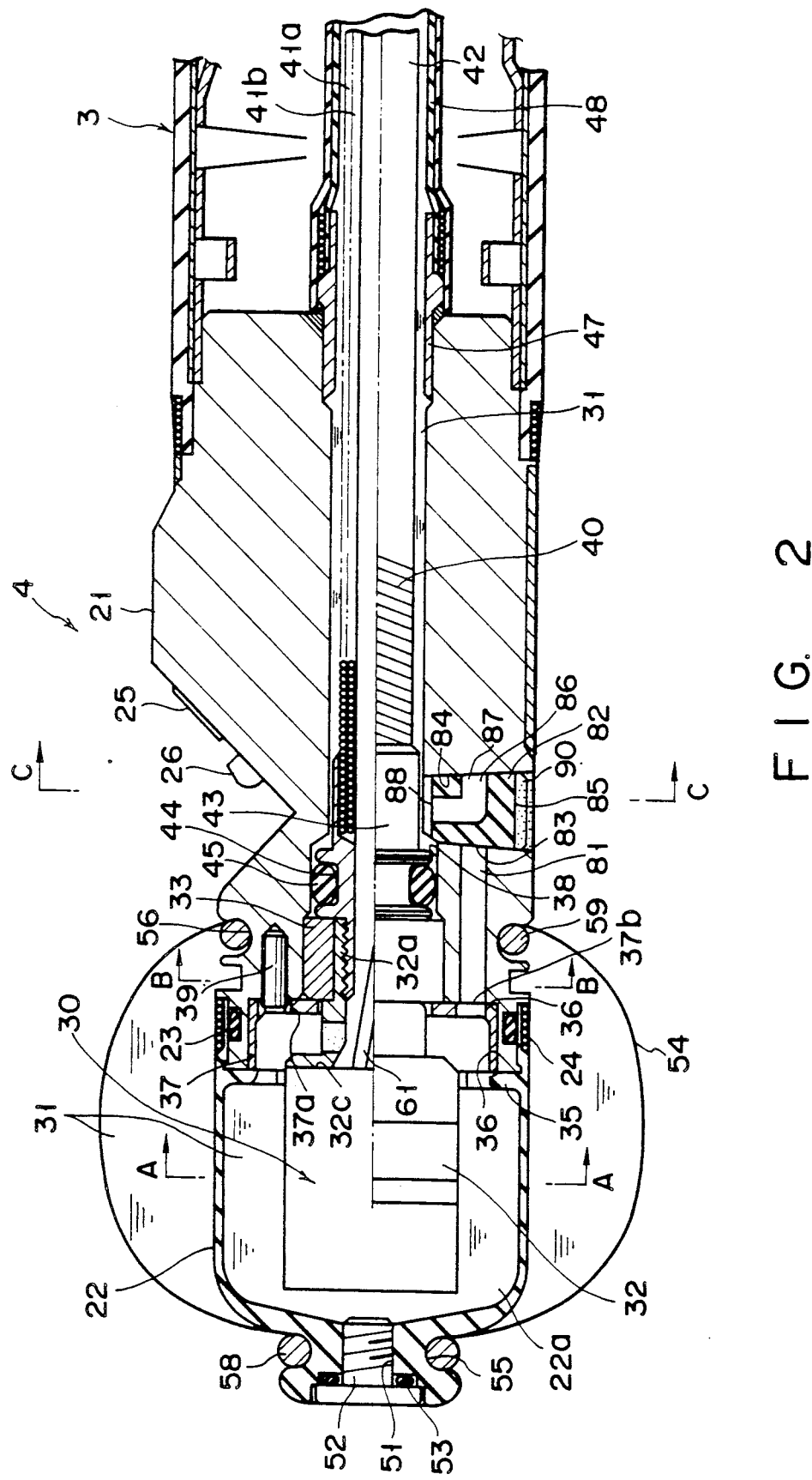
FIG. 2 is a longitudinal view in cross-section showing a distal end portion of an insertion section of an ultrasound diagnostic apparatus of FIG. 1.

The present invention will be explained below with reference to the accompanying drawings.

A first embodiment of the present invention will be explained below with reference to FIGS. 1 to 9.

FIG. 1 shows a whole ultrasound diagnostic apparatus formed integral with an endoscope. In FIG. 1, reference numeral 1 shows an insertion section of larger length comprised of a flexible tube 2, a distal end portion or a tip portion 4 and a bending tube 3 by which the forward end of the flexible tube 2 is connected to the distal end portion. An operation section 5 is connected to the proximal end of the insertion section 1. The operation section 5 includes, for example, an operation knob 6 for bending the bending tube 3, air and water supply buttons 7, and a switch 8. A universal cord 9 and electric cable cord 10 are connected to the operation section 5. A first connector 11 is connected to the forward end of the universal cord 9 and connected to a video processor and illumination light source unit, not shown. A second connector 12 is connected to the forward end of the electric cable cord 10. The connector 12 is connected to an ultrasound diagnostic examination unit, not shown.

FIGS. 2 to 6 show a structure of the distal end portion 4 of the insertion section 1. The distal end portion 4 has a body 21 and a tip cover 22 is mounted on the tip of the body 21 in liquid-tight fashion and provides a housing having a chamber 22a therein. The tip cover 22 is cannonball-like in configuration and is made of a better ultrasound-transmissive material, such as polyethylene. The base end of the tip cover 22 is fitted over the forward end edge of the tip body 21 with a sealing O-ring 23 mounted in place in liquid-tight fashion. A string 24 is wound around the base end edge of the tip cover 22 to achieve a strong, liquid-tight seal.

Figure 3:
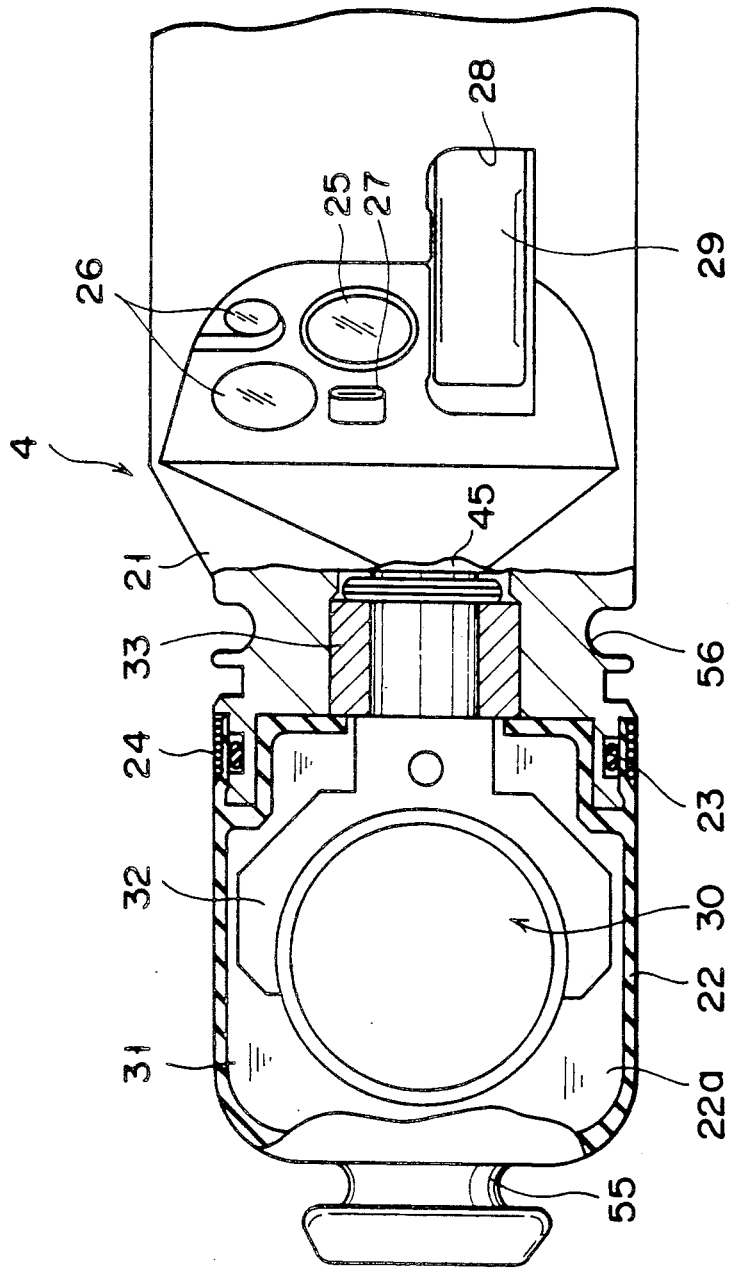
FIG. 3 is a plan view, partly in cross-section, showing the distal end portion of the insertion section of the first embodiment.

On the top surface of the body 21 are provided as shown in FIG. 3, an observation window 25 for an observation system, an illumination window 26 for an illumination optical system, and air/water supply nozzle 27, a forceps opening 28 communicating with a forceps channel, not shown, and a forceps rest 29 provided in the forceps opening 28. A solid-state image sensing device, not shown, is located at an image formation position of the observation optical system, not shown, and an image is electrically picked up by the solid-state image sensing device. A plurality of coaxial cables, not shown, reaching the connector 11 of the universal cord 9 are connected to the solid-state image sensing device. The forceps channel leading to the forceps opening 28 extends via the insertion section 1 to the operation section 5 and from there to a forceps insertion inlet 13.

A probe 30 for conversion is rotatably arranged in the chamber 22a of the tip cover 22 and has an oscillating element for ultrasound transmission and reception. An ultrasound transmitting medium 31, such as liquid paraffin or castor oil, is contained in the tip cover 22. The ultrasonic probe 30 is bonded to a probe holder 32 by an insulating film 32c, such as polyimide. The holder 32 supporting the probe 30 holds its axial section 32a supported by a bearing 33 to allow it to be freely rotated in the tip cover 22. The probe 30 has a rotation center parallel to the longitudinal direction of the insertion section 1. A ring-like spacer member 37 is fitted in place between a flange 35 inwardly formed on the rear end of the tip cover 22 and the bottom surface of a circumferential groove 36 formed on the inner surface of the forward end of the body 21. The bearing 33 is fitted into the forward end portion of a through hole 38 provided in the body 21, and is fixed in place while being pressed by the spacer member 37 against the groove 60. The spacer member 37 has two holes 37a and 37b formed in an axial symmetry. A pin 39 is mounted in the body 21 and fitted into the hole 37a so that the spacer member 37 is fixed in place. The flange 35 is provided not wholly around the circumference of the tip cover and a cutout 35a is partially so provided in the flange that, upon the fitting of the tip cover 22 into the body 21, the probe may not abut against the probe holder 32.

The probe holder 32 is connected to the forward end of a hollow, flexible drive shaft 40 which is rotated by a drive source, such as a motor, provided on the side of the operation section 5. The drive shaft 40 comprises, as shown in FIG. 2, a flexible section 42 comprised of two cylindrical layers, that is, two tightly-coiled cylinders 41a and 41b, and a cylindrical, rigid, forward end axial member 43 connected to the forward end of the flexible section 42. The axial member 43 is securely connected to the probe holder 32 in liquid-tight fashion by threading the axial section 32a of the probe holder 32 into the forward end axial member 43. The axial section 32a of the probe holder 32 is cylindrical in configuration and communicates with the cylindrical interior of the flexible section 42. An annular groove 44 is formed in the outer periphery of the rear end portion of the forward end axial member 43. An O-ring (or an X ring) 45 is fitted into the annular groove 44 and made of an elastic material as a sealing member, achieving a seal between the outer periphery of the forward end axial member 43 and the inner surface of the through-hole 38 of the body 21. That is, a liquid-tight sealing means (first sealing means) is provided between the interior of the chamber 22a of the tip cover 22 and the forward end portion of the passage through which the drive shaft 40 passes. The sealing means has a function of preventing an ingress of air bubbles and a foreign matter, such as dust, from behind the passage through which the drive shaft 40 passes into the tip cover 22.

The passage through which the drive shaft 40 passes is comprised of a through-hole 38 and a guide tube 48 communicating with the through-hole 38 and connected by a connection pipe 47 to the body 21 in liquid-tight fashion. The guide tube 48 is formed of a flexible tube, such as urethane, to provide a water-tight structure.

The drive shaft 40 extends backward via the through hole 38 and guide tube 48 connected to the rear end of the through hole 38. An ultrasound transmitting medium 31 is hermetically filled int eh interior of the drive shaft 40 as well as the interior of the through hole 38 and guide tube 48.

An opening 51 for filling the ultrasound transmitting medium 31 is formed at the central portion of a distal end of the tip cover 22. A sealing screw 52 is threaded into the opening 51 to compress an O-ring 53 therebetween. By so doing it is possible to provide a seal there. Balloon latching sections 55 and 56 are provided, as annular grooves, on the outer peripheral surfaces of the forward and backward end portions of the tip cover 22. The forward and backward edges of a balloon 54 are fitted into the balloon latching sections 55 and 56, respectively, by fastening rings 58 and 59 in liquid-tight fashion. By so doing, the balloon 54 covers the outer periphery of the tip cover 22 in liquid-tight fashion. The interior of the balloon 54 is connected to a water supply passage and water drain passage, not shown, to supply and drain water. The water supply passage and water drain passage are connected via the insertion section 1 and operation section 5 to the universal cord 9 and from there to water supply/drain devices, not shown, via the connector 11. The water supplying draining operation can be done by the operation section 5.

A signal cable 61 passes through the drive shaft 40 which is connected to the ultrasonic probe 30. The signal 61 is connected from the rear end of the insertion section 1 via the operation section 5 and electrical cable cord 10 to the connector 12 and from there to a transmitting/receiving circuit in an ultrasound observation device, not shown.

Figure 7:
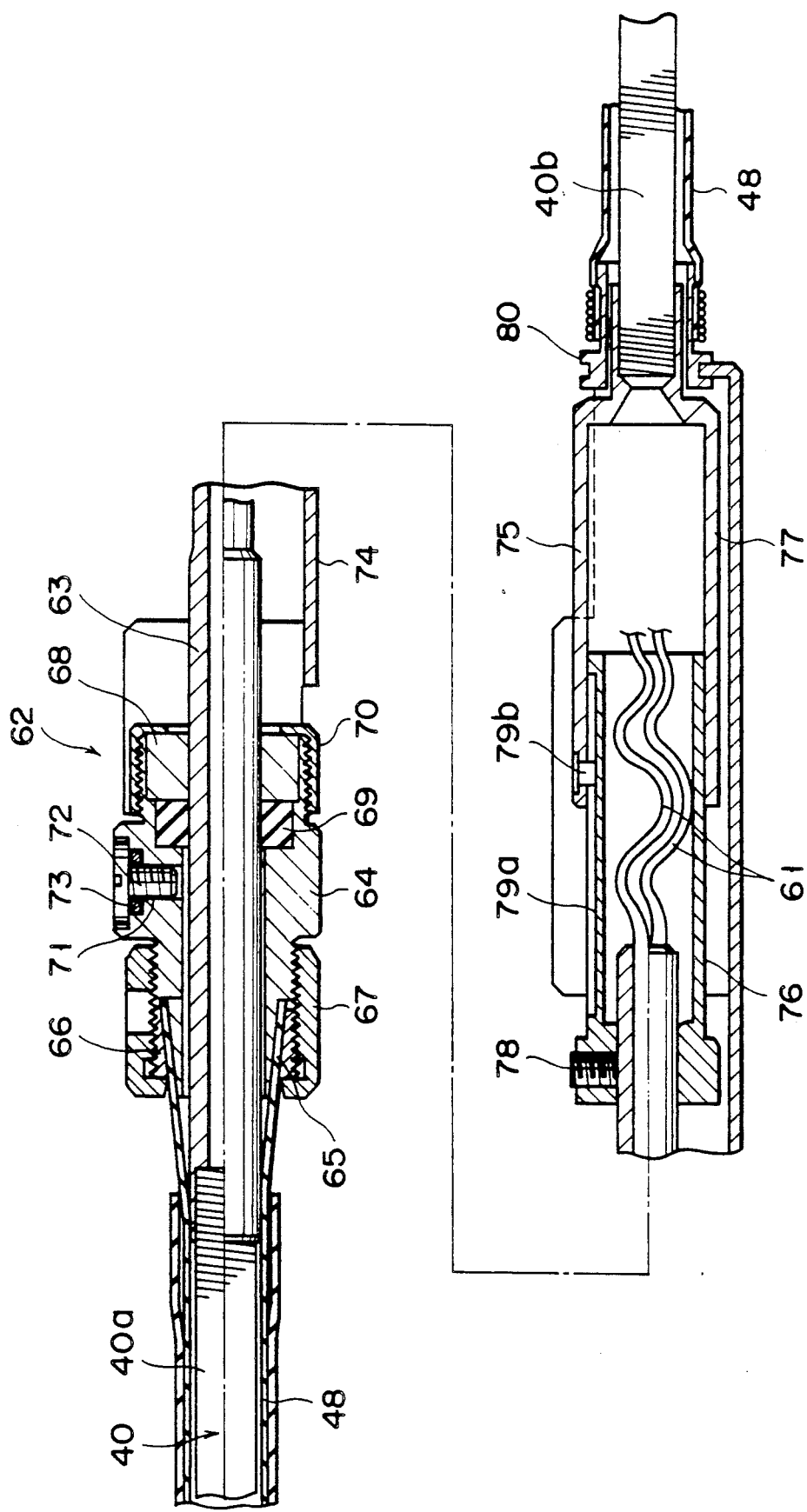
FIG. 7 is a longitudinally sectional view showing a sealing section of a guide tube of the first embodiment.

In the insertion section 1 of the ultrasound diagnostic apparatus, a shaft sealing section (second sealing means) 62 are provided partway of the drive shaft 40 and guide tube 48, as shown in FIG. 7. A forward drive portion 40a of the drive shaft 40 has its rear end connected to the forward end of the sealing shaft 63 and a cylindrical sealing holder 64 is fitted over the shaft 63. The rear end portion of the guide tube 48 is fitted over a tapering outer periphery 65 formed on the forward end of the sealing holder 64. The rear end portion of the guide tube 48 is pushed down by a push-down ring 66 having a corresponding inner taping surface, so that a liquid-tight connection is provided there. The hold-down ring 66 is clamped to the forward end portion of the sealing holder 64 by a fastening clamp ring 67. A bearing 68 rotatably holding the shaft 63 and sealing member 69 slidably contacting with the outer surface of the shaft 63 in liquid-tight fashion is provided within the rear end portion of the sealing holder 64. A fixing ring 70 is threaded over the outer periphery of the rear end portion of the sealing holder 64 to hold the bearing 68 and sealing member 69 in place. It is thus possible to seal the rear end portion of the forwardly positioned guide tube 48 in liquid-tight fashion. An opening 71 is provided in the wall of the sealing holder 64 and communicates with the rear end portion of the forwardly positioning guide tube 48. A sealing screw 72 is threaded into the opening 71 and an O-ring 73 for sealing is located between the inner surface of the opening 71 and the screw 72 The ultrasound transmitting medium 31 sealing the guide tube 48 does not leak out of the tube 48. The sealing holder 64 is held by a support frame 74 and a seal is achieved in the sealing shaft 63 communicating with the signal cable 61.

The rear end portion of the sealing shaft 63 is connected to a coupling cylinder 75 which is rotatable relative to the support frame 74. The coupling cylinder 75 comprises a forward cylindrical section 76 and rearward cylindrical section 77. The sealing shaft 63 is fitted into the forward cylindrical section 76 and secured to the forward cylindrical section 76 by a set screw 78. The rear end portion of the forward cylindrical section 76 is slidable relative to the rearward cylindrical section 76. A guide groove 79a is formed in the outer periphery of the forward cylindrical section 76 such that it extends along the axial direction of the forward cylindrical section 76. A guide groove 79a is provided in the rear end portion of the rearward cylindrical section 76 such that it engages with a guide pin 79b provided in the forward end portion of the cylindrical section 77. Thus the forward cylindrical section 76 and rearward cylindrical section 77 can be slidably moved, in their axial direction, relative to each other without being rotated, so that the coupling cylinder 75 can be retracted along its axial direction and transmit a rotational force.

The forward end of a rearward drive shaft 40b leading to the drive shaft 40 is securely coupled to the rearward cylindrical section 77. The rearward drive shaft 40b is inserted into the rear end portion of the guide tube 48 and the forward end portion of the rearward guide tube 48 is mounted on the support frame 74 by a metal fitting 80.

At the body 21 of the insertion section 1, a communication passage 81 for bypassing is provided to allow the chamber 22a of the tip cover 22 to communicate with the through hole 38, partway behind the O-ring 45, via a hole 37b located at other than the place where the spacer member 37 is located. The communication passage 81 has a rear open end on the guide tube 48 side and at that outer periphery of the forward end axial member 43 which is located as near to the O-ring 45 as possible.

The communication passage 81 has a means for opening and closing the passage on its partway, that is, a passage opening/closing member 82 on its partway across the communication passage 81. The passage opening/closing member 82 is made of plastics such as filler-containing teflon (Rulon), having a slightly inclined, outer taper surface 83. A valve seat hole 84 is provided in a direction transverse to the communication passage 81 such that it is located partway of the communication passage 81 with the passage opening/closing member 82 therebetween. The valve seat hole 84 extends through the side wall of the body 21 and has a tapered inner surface. The passage opening/closing member 82 is tightly fitted into the valve seat hole 84. The passage opening/closing member 82 has a cutout 85 in its outer head into which, for example, a driver can be inserted for rotation.

Figure 8:
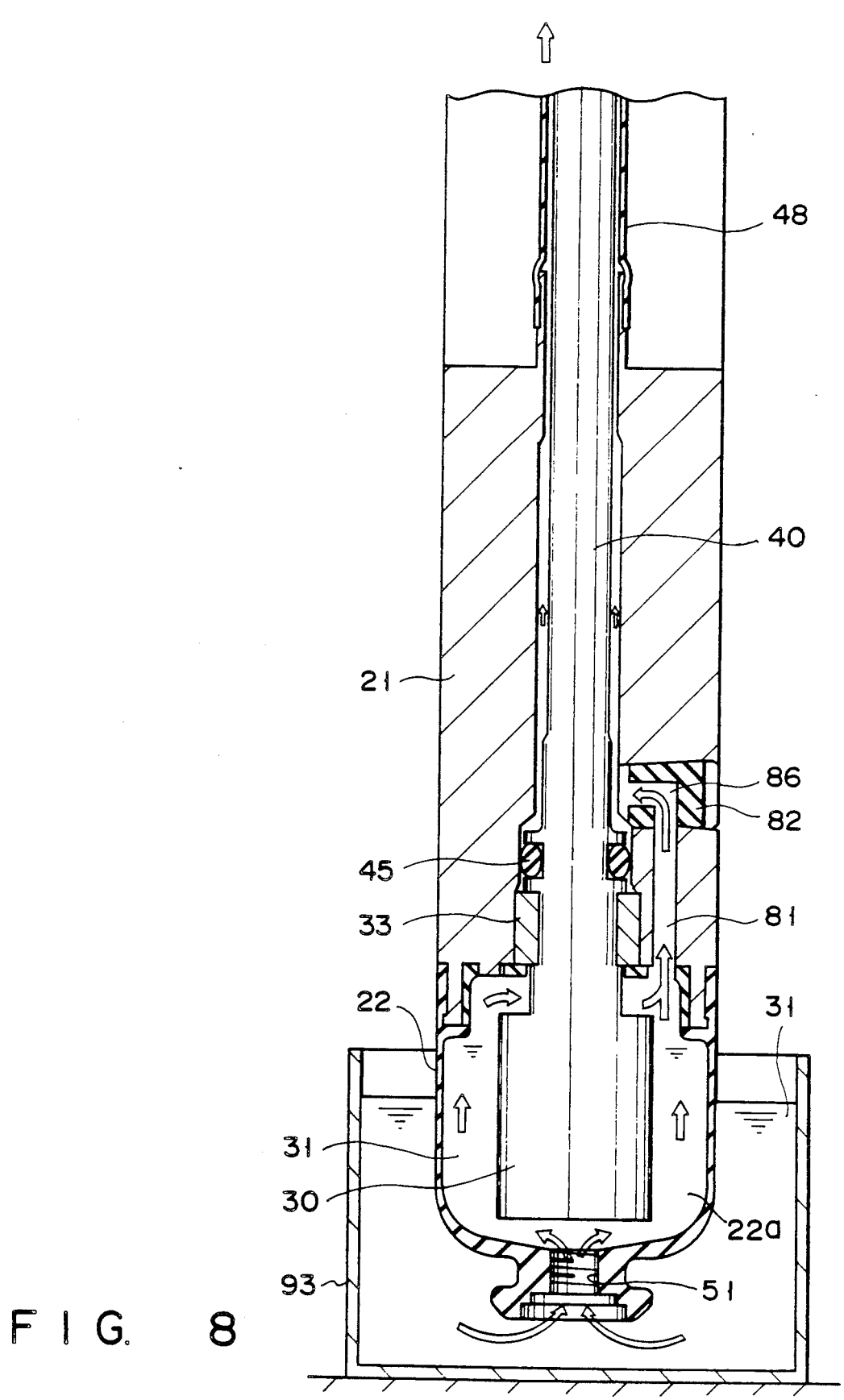
FIG. 8 is a view explaining the filling of an ultrasound transmitting medium according to the present invention.

A curved hole 86 for switching is formed in the passage opening/closing member 82 as shown in FIG. 2. One end of the curved hole 86 is opened at the outer periphery of the passage opening/closing member 82 such that it can be selectively connected to the communication passage 81 when the member 82 is rotated. The other end 88 of the hole 86 is normally opened into the through hole 38 leading to the guide tube 48. That is, when the member 82 is rotated, the end 87 of the hole 86 can be switched from a position in which the passage 81 is blocked by the inner surface of the valve seat 84 as shown in FIG. 2 to a position 180° displaced from the aforementioned position, that is, to a position in which the end 87 of the hole 86 is connected to the communication passage 81 as shown in FIG. 8. Stated in another way, the passage opening/closing member 82, being rotated, can selectively take one of a position where its open end 87 communicates with the passage 81 and a position where its open end 87 is blocked.

As shown in FIG. 6, the passage opening/closing member 82 is fixed to the distal end body 21 by a head of a slip-out preventing screw 89. In this state, the member 82 and the screw head are sealed by a sealant 90.

In the ultrasound diagnostic apparatus, the interior of the tip cover 22 containing the probe 30 is blocked by the O-ring 45 relative to the through-hole 38 and guide tube 48, preventing an ingress of an air bubbles and a foreign matter 92, such as dust 92, from the through hole 38 and guide tube 48 through which the drive shaft 40 passes into the tip cover 22. It is thus possible to prevent an ultrasound beam from being disturbed or damped by the air bubbles 91 and dust 92 and hence to obtain a better ultrasound image.

Figure 9:
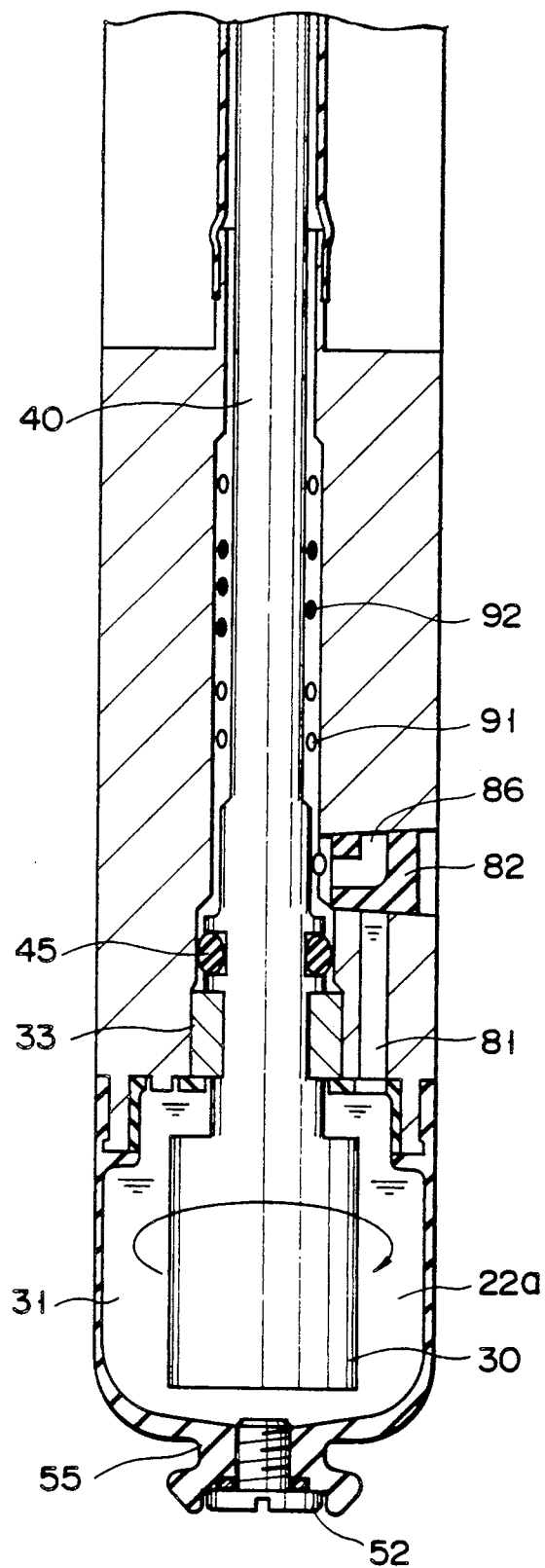
FIG. 9 is a longitudinal view, in cross-section, showing an insertion section of the apparatus of the present invention after the ultrasound transmitting medium has been filled.

Filling an ultrasound transmitting medium 31 into the tip cover 22 and guide tube 48 and sealing it there will be explained below with reference to FIGS. 8 and 9. First the sealing screw 52 is removed from the tip cover 22 to expose the opening 51 of the tip cover 22 as shown in FIG. 8. The open end 87 of the curved hole 86 communicates with the communication passage 81 by detaching the slip-out preventing screw 89 from the apparatus, turning the passage opening/closing member 82 through an angle of 180° and aligning the open end 87 with the communication passage 81. By so doing, the interior of the tip cover 22 is connected to the interior of the through hole 38 and guide tube 48 through which the drive shaft 40 passes This connection can be done without passing a sealed section provided by the O-ring 45.

The ultrasound diagnostic apparatus is held upright with the tip of the tip cove 22 down as shown in FIG. 8 and immersed into a container 93 held with a degassed medium, that is, the ultrasound transmitting medium 31. In this state, the sealing screw 72 and sealing O-ring 73 as shown in FIG. 7 are detached from the shaft sealing section 62. A forward-end connector of a suction tube connected to a suction device, not shown, is connected to the opening 71. Upon the action of suction by the suction tube, the ultrasound transmitting medium 31 in the container 93 is sucked into the tip cover 22 and flows past the communication passage 81 and switching hole 86 into the through-hole 38 at the distal end body 21. A continued suction allows the interior of the guide tube 48, through which the drive shaft 40 passes, to be filled with the ultrasound transmitting medium 31 throughout.

After the interior of each associated part is so filled with the ultrasound transmitting medium 31, the sealing screw 52 is mounted in the opening 51 of the tip cover 22 in the ultrasound transmitting medium 31 to achieve a seal at the opening 51 of the tip cover 22. Then the passage opening/closing member 82 is turned through the angle of 180° to move the open end 87 of the passage opening/closing member 82 out of alignment with the communication passage 81 whereby the communication passage 81 is blocked. The slip-out preventing screw 89 is mounted in the distal end body 21 and hence relative to the passage opening/closing member 82 as shown in FIG. 6 to secure the member 82 in place. After the suction tube has been removed at the shaft sealing section 62, the sealing screw 72 is threaded into the opening 71 with the O-ring 73 held in place to achieve a seal. In this way, the ultrasound transmitting medium 31 is occupied in the interior of the tip cover 22 and in the interior of the through-hole 38 and guide tube 48 through which the drive shaft 40 passes. Therefore, the filling operation is simpler to perform. After this is done, the communication passage 81 is blocked by the passage opening/closing member 82, completely sealing the interior of the tip cover 22 from the rest of the apparatus with the ultrasound transmitting medium 31 so filled.

Generally, air bubbles 91 are liable to be produced in the interior of the drive shaft 40 and in the guide tube 48 through which the drive shaft 40 passes and a foreign matter 92, such as dust and tiny powders worn off a surface, is also liable to remain there. According to the present invention, the interior of the tip cover 22 is completely blocked from the guide tube 48 side through which the drive shaft 40 passes, thereby preventing a ingress of the air bubbles 91 and foreign matter 92 into the interior of the tip cover 22. It is, therefore, possible to prevent the transmit/receive ultrasound wave from being scattered or damped and hence to positively prevent the ingress of air bubbles or foreign matter which would otherwise provide a bar to obtaining a better ultrasound image. As a result, a better ultrasound image can be acquired over an extended period of time.

Figure 10:
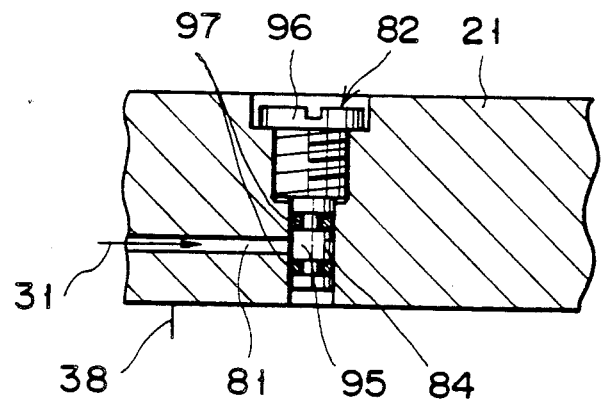
FIG. 10 is a cross-sectional view showing a portion of an opening/closing means of a second embodiment of the present invention with a communication passage sealed.
Figure 11:
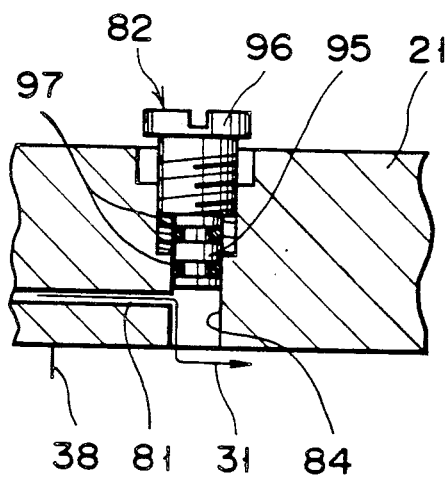
FIG. 11 is a cross-sectional view showing the portion of the opening/closing means of FIG. 10 with the communication passage opened.

FIGS. 10 and 11 show a second embodiment of the present invention. The second embodiment is similar to the first embodiment except that a different means is provided for opening and closing the aforementioned communication passage 81. In the second embodiment, a passage opening/closing member 82 has a screw member 96 threaded into the distal end body 21 having a valve section formed on its inner end portion. The valve section 95 of the screw member 96 is threaded, partway of the connection passage 81, into a valve seat hole 84 formed relative to the center axis of the communication passage 81 and is slidable in the direction of the center axis of the communication passage 81. A pair of O-ring 97 97 are provided at a given interval on the outer surface of the valve section 95. As shown in FIG. 10, the valve section 95 is held in place in the valve seat hole 84 with the screw member 96 placed in an advanced state to block the communication passage 81. With the screw member 96 partway retracted as shown in FIG. 11, the valve section 95 of the screw member 96 is located in communication with the communication passage 81. That is, the rotation of the screw member 96 moves the valve section 95 into and out of fluid communication with the valve hole 84 to open and close the communication passage 81. Therefore, the filling operation of the ultrasound transmitting medium 31 can be done in the same way as in the first embodiment.

In the second embodiment, the screw member 96 serves also as a slip-out preventing screw for the passage opening/closing member, thus eliminating the need for any extra slip-out preventing screw as in the first embodiment. The second embodiment saves the number of component parts required and can be assembled in compact form.

Figure 12:
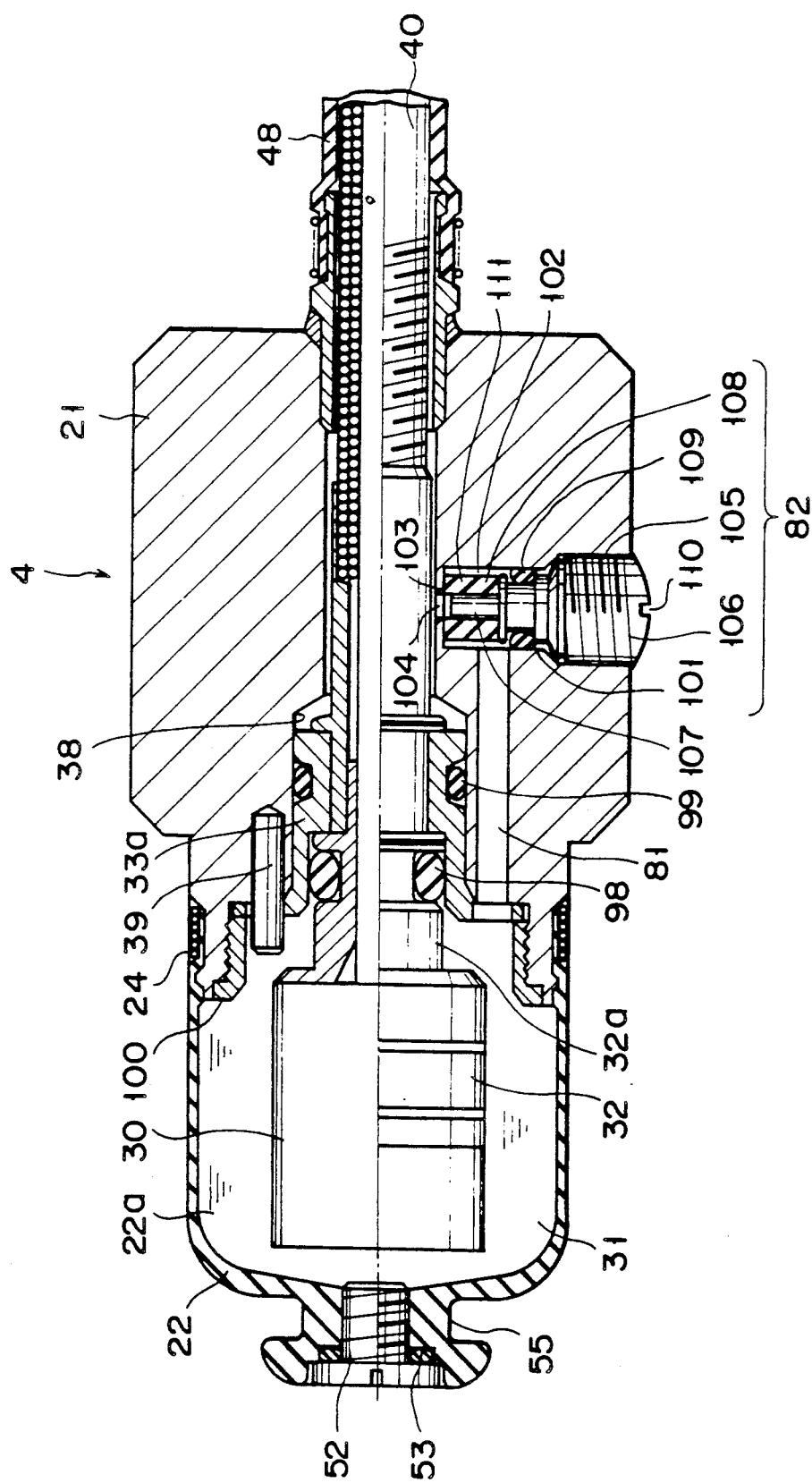
FIGS. 12 and 13 are longitudinally sectional views, in cross section, showing a distal end portion of an insertion section of a third embodiment of the present invention.
Figure 13:
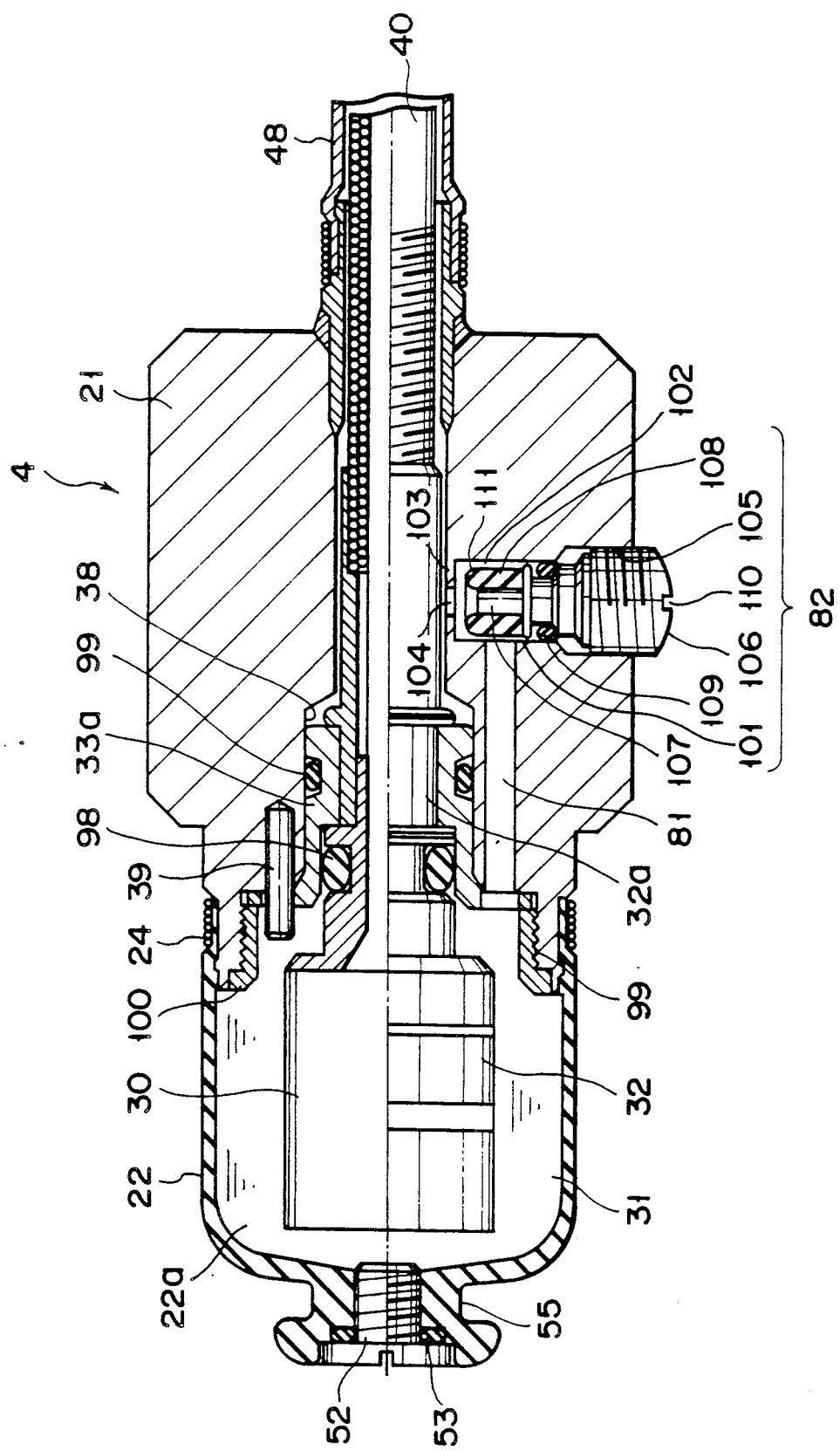
Figure 14:
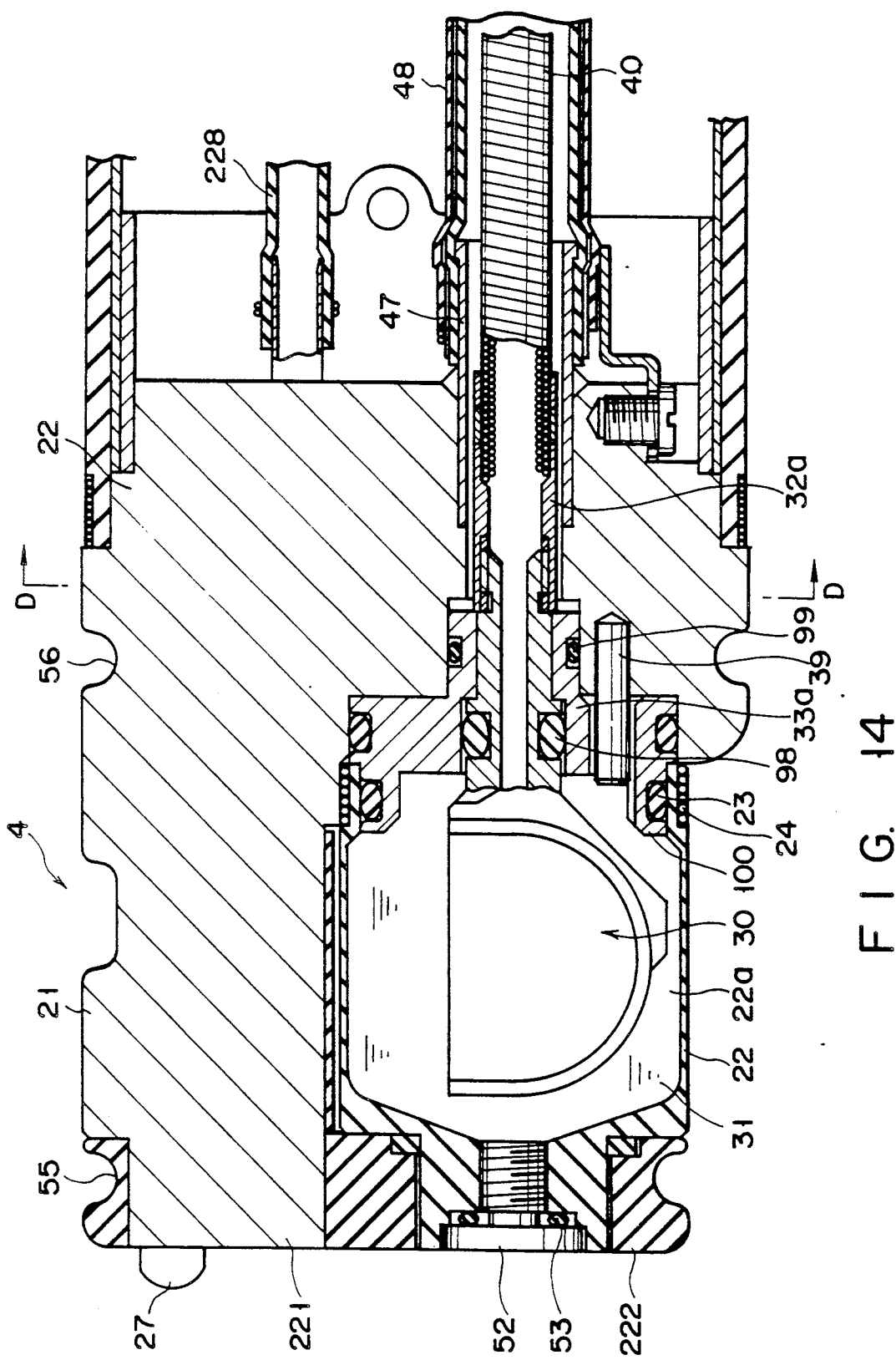
FIG. 14 is a longitudinally sectional view, in cross-section, showing a distal end portion of an insertion section of a fourth embodiment of the present invention.

FIGS. 12 and 13 show a third embodiment of the present invention. The third embodiment has a bearing 33a which provides a modified counterpart compared with the bearing 33 of the first embodiment In the third embodiment, a pair of O-rings 98, 99 are located one on the outer periphery of an axial section 32a of a probe holder 32 and the other on the inner surface of a through-hole 38. The bearing 33a is fixed to a distal end body 21 by a bearing push-down member 100 which is threadedly mounted there.

The bearing 33a and O-rings 98, 99 constitute a bearing unit which serves not only as a bearing per se as in the first embodiment but also as a sealing member.

In the third embodiment, a means for opening and closing the communication passage 81 is different from the counterpart of the preceding embodiments in the following respects.

That is, a fitting hole 101 into which a passage opening/closing member 82 is fitted is provided partway of a communication passage 81. One end of the fitting hole 101 is opened at the outer surface of a distal end body 21 and the other end of the fitting hole 101 provides a valve seat hole 102 constituting part of the communication passage 81. A valve seat wall 103 is provided at the inner end of the valve seat hole 1, that is, at its side facing the through-hole 38 through which a drive shaft 40 passes. A communication hole 103 is provided at the center of the valve seat wall 103 such that it communicates with the through-hole 38 through which the drive shaft 40 passes.

The passage opening/closing member 82 inserted into the fitting hole 101 comprises a screw section 106 threaded into a threaded hole 105 of the distal end body 21, a valve stem section 107 located in the valve seat hold 102 of the fitting hole 101, a cylindrical, elastic sealing member 108 fitted over the outer periphery of the valve stem section 107, and an O-ring 109 fitted on the outer side than the elastic sealing member 108 and sealing the threaded hole 105. A groove 110 engaged by a driver is formed on a head section of the passage opening/closing member 82. Rotating the passage opening/closing member 82 with the groove 110 engaged by the driver causes it to be advanced or retracted, through a threaded engagement of the screw section 106 with the threaded hole 105, in accordance with the direction of its rotation. The elastic sealing member 108 is made smaller in its outer diameter than in the inner diameter of the valve seat hole 102, but equal and greater in its inner diameter to and than the inner diameter of the valve seat hole 102. The elastic sealing member's inner end facing the valve seat wall 103 is somewhat projected beyond the inner end of valve stem section 107 to provide a valve section 111.

Threadably advancing the passage opening/closing member 82 as shown in FIG. 12 causes the valve section 111 of the elastic sealing member 108 to closely abut against the valve seat wall 103 to cover the valve seat hole 102 and hence to block a communication passage 81.

Retracting the passage opening/closing member 82 as shown in FIG. 13, that is, slightly slackening it causes the valve seat 111 of the elastic sealing member 108 to be moved away from the valve seat wall 103 so that the valve seat hole 102 is opened to communicate with the communication passage 81.

The communication opening/closing member 82 can be used to open and close the communication passage 81, that is, the opening/closing means is so provided as set out above, and the filling operation of the ultrasound transmitting member 82 can be performed in the same way as in the preceding embodiment. In the third embodiment, sealing is achieved by pushing the valve section 111 of the elastic sealing member 108 against the valve seat wall 103. Since the passage opening/closing member 82 is moved with a less stroke than in the case where sealing is done with the use of, for example, an O-ring, it can reduce, for example, the diameter of the distal end body 21 to give less pain to the patient.

FIGS. 14 to 18 show a fourth embodiment of the present invention. The fourth embodiment is different from the first through third embodiments in the position and direction, in particular, in which a communication opening/closing member 82 is mounted. Stated in more detail, the passage opening/closing member 82 of the preceding embodiments was mounted in a direction substantially perpendicular to the center axis of a distal end portion 4 and extended from the side portion of the distal end portion 4 toward said center axis. For this reason, the head of the passage opening/closing member 82 was located in the side portion of the distal end portion 4. In the fourth embodiment, as shown in FIGS. 15 to 18, a head of the passage opening/closing member 82 is provided in a tip end face of a distal end body 21 of a distal end portion 4 such that it is oriented in a forward direction.

Figure 16:
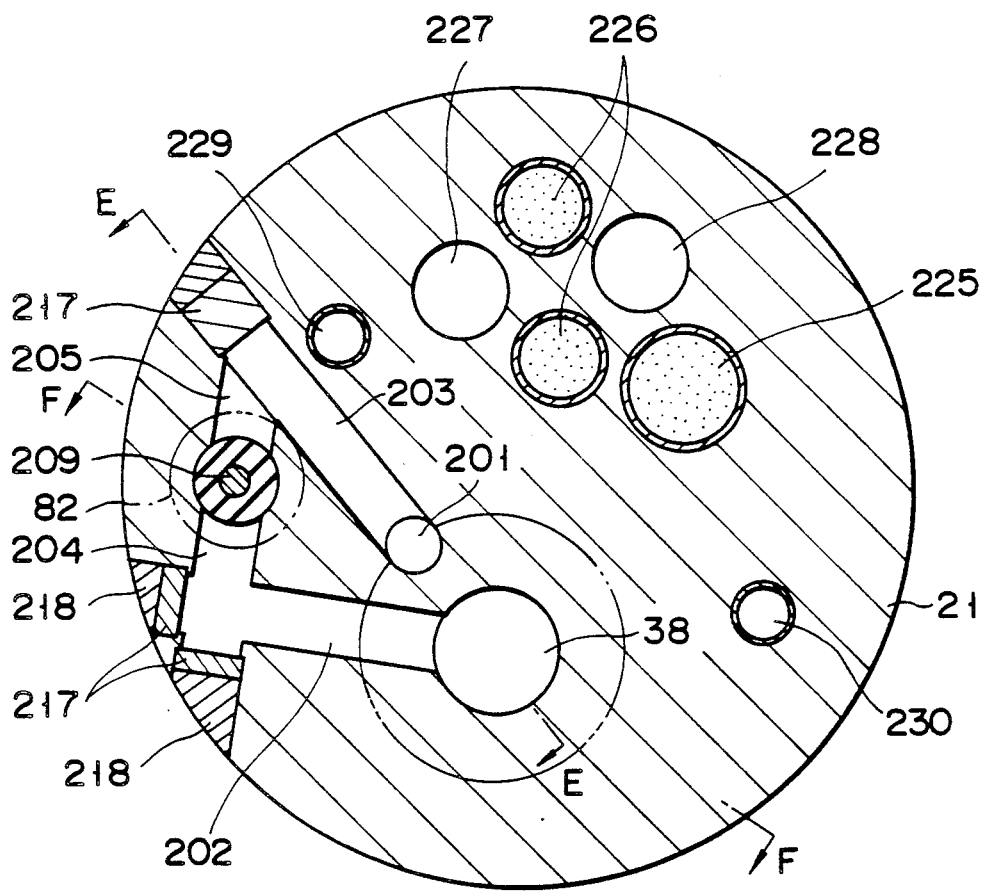
FIG. 16 is a cross-sectional view as taken along line D—D in FIG. 14.
Figure 17:
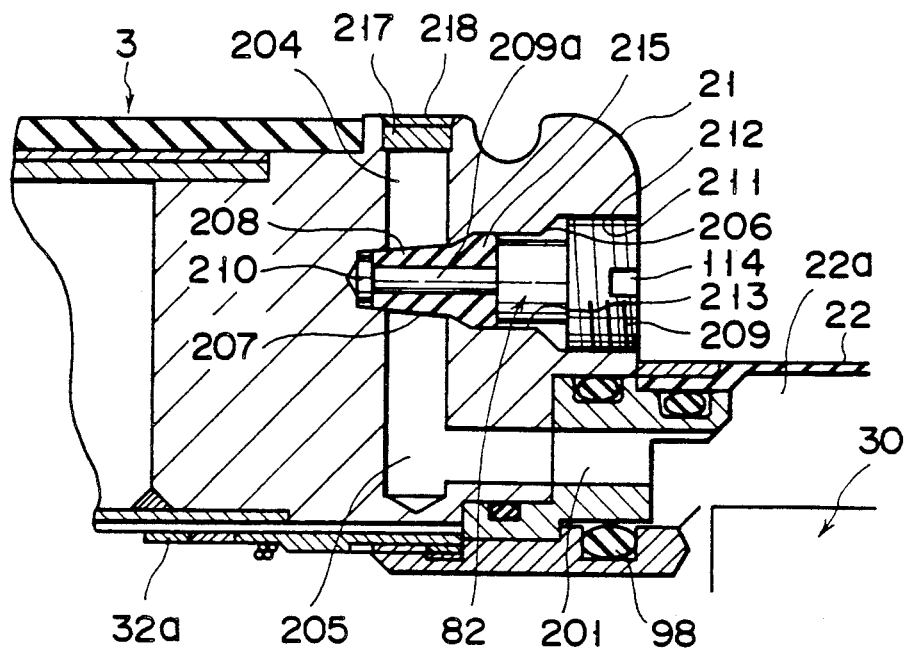
FIGS. 17 and 18 are cross-sectional views as taken along lines E—E and F—F lines in combined format showing the states of different operation.
Figure 18:
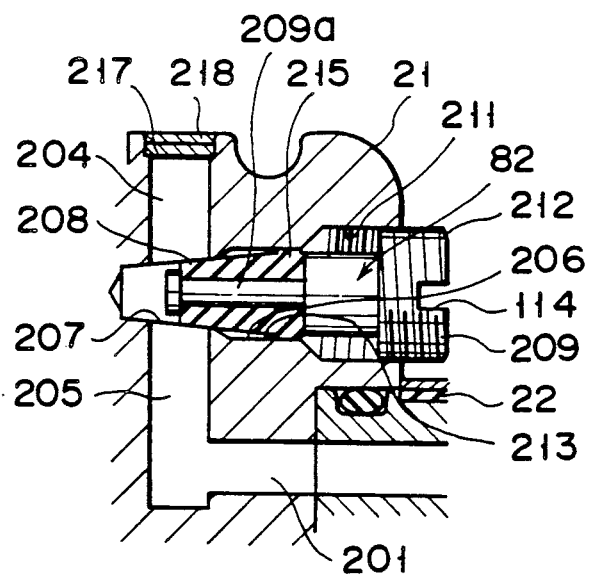

Stated in more detail, as shown in FIGS. 16 to 18, a first communication passage 201 leading to the interior of a tip cover 22 is provided in the distal end body 21 in a forward/backward direction parallel to the distal end portion 4. As shown in FIG. 16, a distal end body 21 has a second communication passage 202 at a side behind on O-ring (sealing member) 45 or 98 in a range of the through-hole 38. As shown in FIG. 16, the two communication passages 201 and 202 communicate with each other via a series array of communication holes 203 and 204 in the distal end body 21, providing a bypass passage 205 for allowing the interior of the tip cover 22 to be connected to the through-hole 38 at the site behind the O-ring 98 and in the range of the through-hole 38 through which the drive shaft 40 passes. An opening/closing means is provided partway of the communication hole 24 of the bypass path 205 and can be opened and closed with the us of a passage opening/closing member 82 as will be set out below.

A fitting hole 206 is provided in the distal end face portion of the distal end body 21 such that it blocks the communication hole 204 of the bypass passage 205 in a manner to extend toward the rotation center axis of the probe 30. The passage opening/closing member 82 is fitted into the fitting hole 206. A tapering valve seat hole 207 is provided in an intersection area of the fitting hole 206 and communication hole 204 as shown in FIGS. 17 and 18. The passage opening/ closing member 82 is mounted in the valve seat hole 207. The passage opening/closing member 82 has a rod-like member 209 whose insertion section's forward end portion is to be wrapped with a tapering tube-like, elastic sealing member 208. The elastic sealing member 208 is firmly wrapped or fitted over a forward end, narrow-diameter section 210 of the rod-like member 209 to provide an integral unit. The elastic sealing member 208 has its tapering outer peripheral section fitted into the valve seat hole 207 having a corresponding tapering portion. An externally threaded section 212 is formed on the external peripheral portion of the passage opening/closing member 82 which is threaded into an internally threaded section 211 formed in the internal wall of the outer end portion of the fitting hole 206. A parallel axial section 209a is formed on an intermediate section of the passage opening/closing member 82. A parallel hole section 213 is provided at a location between the valve seat hole 207 and the internally threaded section 211, that is, at a location of that inner surface portion of the fitting hole 206 facing the parallel axial section 209a and has a diameter greater than the valve seat hole 207 but smaller than the externally threaded section 212. As shown in FIGS. 17 and 18, an engaging groove 114 to be rotatably engaged by a driver is provided on the outer face of a head of the passage opening/closing member 82.

A second sealing member 215 is provided integral with the outer periphery of the rear end portion of the elastic sealing member 208 to provide an annular ridge greater than the tapering outer periphery section. Since the second sealing member 215 is provided integral with the elastic sealing member 208, the sealing members 208 and 215, that is, those sealing parts for sealing the valve hole 207 as will be set out below, are so provided as to have a small length.

A sealing member 217 is fitted over each outer open end portion of the communication passage 202 and passage holes 203 and 204 as shown in FIGS. 16 to 18 and securely held in place with the use of an adhesive agent 218.

Opening and closing the bypass passage 205 with the use of the passage opening/closing member 82 is accomplished as follows:

When the passage is to be closed, the rod-like member 209 is rotated to cause the externally threaded section 212 of the member 82 to threadably advance into the internally threaded section 211 at which time the elastic sealing member 208 is pushed into the valve seat hole 207 as shown in FIG. 17. The outer peripheral portion of the elastic sealing member 208 is closely pushed into the valve seat hole 207 to achieve a seal. By so doing, the elastic sealing member 208 passes across the communication hole 204 to completely shut off that location and hence to block the bypass passage 205. At that time, the elastic sealing member 215 located on the outer periphery of the rear end portion of the elastic sealing member 208 is pushed into the valve seat hole 207 by a step of the "forward end" side of the parallel axial section 209a of the rod-like member 209 to achieve a close seal.

When the passage is to be opened, the rod-like member 209 is rotated back through a threadable engagement of the externally threaded section 212 away from the internally threaded section 211 so that the elastic sealing member 208 is retracted away from the valve seat hole 207 as shown in FIG. 18. As a result, the passage 205 is opened with the elastic sealing member 208 so retracted back from the valve seat hole 207.

According to the fourth embodiment, the bypass passage 205 intersects in a direction of the rotational center axis of the probe 30 so that the opening/closing means using the passage opening/closing member 82 can be located not on the side portion of the distal end portion 4 but on the front face portion as already set out above and the bypass passage 205 is provided at the same cross-section 205. For this reason, there is no need to increase the size of the distal end portion 4 and, at the same time, the passage opening/closing member 82 can gain an adequate stroke. It is thus possible to acquire a better opening/closing characteristic and so on.

According to the present invention, it is possible to shorten a rigid part of the distal end portion 4 to a minimum possible extent, which can improve the insertion performance of the insertion section 1 of the apparatus even if the instrument tip is inserted deep into, for example, the large intestine of the patient.

A portion of the distal end body 21 of the distal end portion 4 is forwardly projected as a projection 221 in a side-by-side relation to the tip cover 22 to provide a direct-viewing type endoscope having endoscopic observation and illumination means at that projection. That is, an observation window 25, illumination window 26, air/water supply nozzle 27, forceps access opening 28, etc., are provided at the distal end face of the projection 221. The side peripheral portion of the distal end face portion of the combined projection 221 and tip cover 22 is wrapped with a distal end surrounding member 222.

In FIG. 16, reference numeral 225 shows an image guide fiber bundle; 226, light guide fiber bundless 227, a channel; 228, an air/water supply passage; 229 a tube passage for supplying deaerated water to the balloon 54; and 230 a tube passage for discharging the deaerated water.

The present invention is not limited to the aforementioned embodiments. For example, without utilizing a suction force of a suction device in the ultrasound transmitting medium filling operation, a jig may be mounted on the present apparatus in place of the sealing screw for sealing the tip cover and then the filling of the ultrasound transmitting medium may be achieved with the use of, for example, a syringe. Although the present embodiment has been explained as using the observation means utilizing the solid state image pickup device, an observation system using the image guide bundle may be employed instead. The present invention can be applied to an apparatus having no endoscopic function. In the present embodiment, the drive shaft may be of a rigid type instead of a flexible one as already set out above.

What is claimed is:

1. An ultrasound diagnostic apparatus which is adapted to be inserted into a body cavity for mechanically scanning said body cavity with an ultrasound beam, to obtain an ultrasound observation image of the body cavity, said ultrasound diagnostic apparatus comprising:

(a) an elongated insertion section having:
    a length;
    a distal end portion that is adapted to be inserted into the body cavity;
    a housing including a chamber positioned at the distal end portion of the elongated insertion section, said chamber having an interior portion therewithin;
    a proximal end portion; and
    a guide passage having a first and second end portion, the first end portion of the guide passage leading to the chamber, said guide passage extending along the length of the elongated insertion section;

(b) a probe for generating an ultrasound beam, said probe being positioned in said chamber of said housing, aid probe having an axis around which said probe is rotatable when positioned in the chamber;

(c) a drive shaft passing through the guide passage and coupled to the probe to transmit a rotational force to the probe;

(d) drive means coupled to said drive shaft;

(e) first sealing means positioned between the interior of said chamber and the first end portion of the guide passage for blocking a communication between the chamber and the first end portion of the guide passage;

(f) second sealing means for sealing the second end portion of the guide passage;

(g) a bypass communication passage having a given length for allowing a communication between the chamber and the guide passage;

(h) bypass opening and closing means for selectively opening and closing the bypass communication passage, said bypass opening and closing means being positioned at the bypass communication passage; and (i) an ultrasound transmitting medium sealed in the chamber and the guide passage.

2. The ultrasound diagnostic apparatus according to claim 1, wherein said bypass opening and closing means comprises:

a valve seat hole provide partway along the given length of said bypass communication passage, said valve seal hole being positioned across from the bypass communication passage; and a rotatable valve member insertable in said valve seat hole, said rotatable valve member having a first rotational position which opens the bypass communication passage and a second rotational position which closes the bypass communication passage.

3. The ultrasound diagnostic apparatus according to claim 1, wherein said bypass opening and closing means comprises:

a valve seat hole provided partway along the given length of said bypass communication passage, said valve seal hole being positioned along an axis of the bypass communication passage; and a valve member insertable in the valve seat hole, said valve member being axially movable between a first position where the valve member is retracted out of said bypass communication passage to open the bypass communication passage and a second position where the valve member is moved into the bypass communication passage to block the bypass communication passage.

4. The ultrasound diagnostic apparatus according to claim 1, wherein said bypass communication opening and closing means comprises:

a valve seat wall provided in said bypass communication passage, said valve seat wall having a communication hole formed therein; and an elastic valve body located opposite the valve seat wall, said elastic valve body being movable toward and away from the valve seat wall, said valve seat body when moved toward the valve seat wall closing the communication hole to block said bypass communication passage, and said valve seat body when moved away from the valve seat wall opening the bypass communication passage.

5. The ultrasound diagnostic apparatus according to claim 1, wherein said bypass opening and closing means comprises:

a valve seat hole provided across a portion of said bypass communication passage in a direction parallel to the rotation axis of said probe; and a valve member provided in the valve seat hole, said valve member having a first and a second operational position such that when said valve member is in he first operational position it allows communication with the bypass communication passage, and when the said valve member is in the second operational position it blocks tbe bypass communication passage.

6. An ultrasound diagnostic apparatus which is adapted to be inserted into a body cavity for mechanically scanning said body cavity with an ultrasound beam, to obtain an ultrasound observation image of the body cavity, said ultrasound diagnostic apparatus comprising:

(a) an elongated insertion section having:
    a length;

a distal end portion that is adapted to be inserted into the body cavity;

a housing including a chamber positioned at the distal end portion of the elongated insertion section;

a proximal end portion; and a guide passage having a first and second end portion, the first end portion of the guide passage leading to the chamber, said guide passage extending along the length of the elongated insertion section;

(b) a probe for generating an ultrasound beam, said probe being positioned in said chamber of said housing, said probe having an axis around which said probe is rotatable when positioned in the chamber;

(c) a drive shaft coupled to the probe to transmit a rotational force to the probe;

(d) drive means coupled to said drive shaft to rotate said drive shaft;

(e) first sealing means for blocking a communication between the chamber and the first end portion of the guide passage;

(f) second sealing means for sealing the second end portion of the guide passage;

(g) a bypass communication passage having a given length for allowing a communication between the chamber and the guide passage;

(h) bypass opening and closing means for selectively opening and closing the bypass communication passage, said bypass opening and closing means being positioned at the bypass communication passage; and (i) an ultrasound transmitting medium sealed in the chamber and in the guide passage.

7. The ultrasound diagnostic apparatus according to claim 6, wherein said bypass opening and closing means comprises:

a valve seat hole provided partway along the given length of said bypass communication passage, said valve seal hole being positioned across from the bypass communication passage; and a rotatable valve member insertable in said valve seat hole, said rotatable valve member having a first rotational positional which opens the bypass communication passage and a second rotational position which closes the bypass communication passage.

8. The ultrasound diagnostic apparatus according to claim 6, wherein said bypass opening and closing means comprises:

a valve seat hole provided partway along the given length of said bypass communication passage, said valve seal hole being positioned along an axis of the bypass communication passage; and a valve member insertable in the valve seat hole, said valve member being axially movable between a first position where the valve member is retracted out of said bypass communication passage to open the bypass communication passage and a second position where the valve member is moved into the bypass communication passage to block the bypass communication passage.

9. The ultrasound diagnostic apparatus according to claim 6, wherein said bypass communication opening and closing means comprises:

a valve seat wall provided in said bypass communication passage, said valve seat wall having a communication hole formed therein; and an elastic valve body located opposite the valve seat wall, said elastic valve body being movable toward and away from the valve seat wall, said valve seat body when moved toward the valve seat wall closing the communication hole to block said bypass communication passage, and said valve seat body when moved away from the valve seat wall opening the bypass communication passage.

10. The ultrasound diagnostic apparatus according to claim 6, wherein said bypass opening and closing means comprises:

a valve seat hole provided across a portion of said bypass communication passage in a direction parallel to the rotation axis of said probe: and a valve member provided in the valve seat hole, said valve member having a first and a second operational position such that when said valve member is in the first operational position it allows communication with the bypass communication passage, and when the said valve member is in the second operational position it blocks the bypass communication passage.

* * * * *